US011149284B2

(12) United States Patent
Kang et al.

(10) Patent No.: US 11,149,284 B2
(45) Date of Patent: Oct. 19, 2021

(54) TRANSGENIC CLONED PIGLET EXPRESSING HUMAN PROINSULIN AND METHOD OF PRODUCING THE SAME

(71) Applicant: MGENPLUS CO., LTD., Seoul (KR)

(72) Inventors: Jung-Taek Kang, Seoul (KR); Bumrae Cho, Seoul (KR); Su Jin Kim, Gyeonggi-do (KR); Dal Young Ji, Gyeonggi-do (KR); Eun Jin Lee, Gyeonggi-do (KR); Sun Mi Ahn, Gyeonggi-do (KR); Jin Seok Lee, Seoul (KR)

(73) Assignee: MGENPLUS CO., LTD., Seoul (KR)

( * ) Notice: Subject to any disclaimer, the term of this patent is extended or adjusted under 35 U.S.C. 154(b) by 0 days.

(21) Appl. No.: 15/983,989

(22) Filed: May 18, 2018

(65) Prior Publication Data

US 2019/0093124 A1    Mar. 28, 2019

(30) Foreign Application Priority Data

Sep. 26, 2017 (KR) .......................... 10-2017-0124507

(51) Int. Cl.
*C12N 15/85* (2006.01)
*C12N 15/877* (2010.01)
*A01K 67/027* (2006.01)

(52) U.S. Cl.
CPC ...... *C12N 15/8509* (2013.01); *A01K 67/0276* (2013.01); *A01K 67/0278* (2013.01); *C12N 15/8778* (2013.01); *A01K 2217/052* (2013.01); *A01K 2217/072* (2013.01); *A01K 2227/108* (2013.01); *A01K 2267/01* (2013.01); *A01K 2267/0362* (2013.01); *C12N 2015/8518* (2013.01)

(58) Field of Classification Search
CPC ............ C12N 15/8509; C12N 15/8778; C12N 2015/8518; A01K 67/0276; A01K 2217/052; A01K 2227/108; A01K 2267/01

USPC .......................................................... 800/17
See application file for complete search history.

(56) References Cited

U.S. PATENT DOCUMENTS 9,339,519 B2    5/2016    Ayares

FOREIGN PATENT DOCUMENTS

| KR | 1020070045819 A | 5/2007 |
| KR | 1020150034094 A | 9/2014 |
| KR | 101748575 B1 | 6/2017 |
| WO | 2011/020120 A1 | 2/2011 |
| WO | 2013/167743 A1 | 11/2013 |

OTHER PUBLICATIONS

Meirelles, Genomics, 2001, 158:351-356).*
Fehilly et al (1985), J. Reprod. Fert., 74:215-221.*
Mehta, 2017, Agricultural Reviews, 38:129-136.*
Cho (2007, Developmental Dynamics, 236:3369-3382).*
Wijkstrom, Martin, et al. "Glucose metabolism in pigs expressing human genes under an insulin promoter." Xenotransplantation 22.1 (2015): 70-79.
Qian, Xi, et al. "Production of recombinant human proinsulin in the milk of transgenic mice." Scientific reports 4 (2014): 6465.

* cited by examiner

*Primary Examiner* — Valarie E Bertoglio
(74) *Attorney, Agent, or Firm* — Wood, Phillips, Katz, Clark & Mortimer

(57) ABSTRACT

A transgenic cloned piglet expressing human proinsulin and a method of preparing the same, and more particularly, to a recombinant vector for human proinsulin expression, a genetically modified cell line into which the recombinant vector is introduced, a transgenic cloned piglet expressing human proinsulin, and a method of producing the same.

7 Claims, 8 Drawing Sheets
Specification includes a Sequence Listing.

SEQUENCE LISTING

```
<160> NUMBER OF SEQ ID NOS: 13

<210> SEQ ID NO 1
<211> LENGTH: 396
<212> TYPE: DNA
<213> ORGANISM: Homo sapiens

<400> SEQUENCE: 1
gccatcaagc aggtctgttc caagggcctt tgcgtcagat cactgtcctt ctgccatggc      60
cctgtggatg cgcctcctgc ccctgctggc gctgctggcc ctctggggac ctgacccagc     120
cgcagccttt gtgaaccaac acctgtgcgg ctcacacctg gtggaagctc tctacctagt     180
gtgcggggaa cgaggcttct tctacacacc caagacccgc cggaggcag aggacctgca      240 ggtggggcag gtggagctgg gcggggggccc tggtgcaggc agcctgcagc ccttggccct    300
ggaggggtcc ctgcagaagc gtggcattgt ggaacaatgc tgtaccagca tctgctccct    360
ctaccagctg gagaactact gcaactagac gcagcc                              396

<210> SEQ ID NO 2
<211> LENGTH: 1639
<212> TYPE: DNA
<213> ORGANISM: Artificial
<220> FEATURE:
<223> OTHER INFORMATION: Insulin nucleotide fragment

<400> SEQUENCE: 2
agatcttcta gagagttctt ctgtttgcta gataagaaat cctggtctgc catcccagca      60
ggcccaggct gtttaagtta ctagataaca gggttgttat tgatcctatt attattattt     120
tttctactct tcctgattcc ctgaagtcca agggacgttt ttttctatta agaatgattt     180
tttgtttaaa aaaaaaaaa gagtccttgt tgtgtcgcta gctggtctgt gacagataga     240
gcccagagct gcctcagtgc cctttactca ggagtgggag aacagaaagt aaataagcca     300
gagcccagag cactcttagt catctggatg gctcagcgct gggcccagca cttgcaaatg     360
ctggctcctc ccggactccc ctgttagccc catgttgtta accagtttaa cattcccta     420 tcacatgctc atgtgggcag aattaagtgg aattagctaa caaattatat aaaattcatt     480 taccttttaaa ctagtcgaca ccaaatcagg aacagaaaga gtcaaggatc ccccaaccac   540
tccaagtgga ggctgagaaa ggttttgtag ctgggtagag tatgtactaa gagatggaga    600
cagctggctc tgagctctga agcaagcacc tcttatggag agttgctgac cttcaggtgc    660
aaatctaaga tactacagga gaatacacca tggggcttca gcccagttga ctcccgagtg    720
```

```
ggctatgggt tgtggaagg agagatagaa gagaagggac ctttcttctt gaattctgct      780
ttccttctac ctctgagggt gagctggggt ctcagctgag gtgaggacac agctatcagt      840
gggaactgtg aaacaacagt tcaagggaca aagttactag gtcccccaac aactgcagcc      900
tcctggggaa tgatgtggaa aaatgctcag ccaaggacaa agaaggcctc accctctctg      960
agacaatgtc ccctgctgtg aactggttca tcaggccacc caggagcccc tattaagact     1020
ctaattaccc taaggctaag tagaggtgtt gttgtccaat gagcactttc tgcagaccta     1080
gcaccaggca agtgtttgga aactgcagct tcagcccctc tggccatctg ctgatccacc     1140
cttaatggga caaacagcaa agtccagggg tcagggggg gtgctttgg actataaagc       1200 tagtggggat tcagtaaccc ccagccctaa gtgaccagct acagtcggaa accatcagca     1260
agcaggtaag cttgatatcg gtaccatggc cctgtggatg cgcctcctgc ccctgctggc     1320
gctgctggcc ctctggggac ctgacccagc cgcagccttt gtgaaccaac acctgtgcgg     1380
ctcacacctg gtggaagctc tctacctagt gtgcggggaa cgaggcttct tctacacacc     1440
caagacccgc cggaggcag aggacctgca ggtggggcag gtggagctgg gcggggccc       1500 tggtgcaggc agcctgcagc ccttggccct ggaggggtcc ctgcagaagc gtggcattgt     1560
ggaacaatgc tgtaccagca tctgctccct ctaccagctg gagaactact gcaactaggc     1620
ggccgcgttt aaactcgag                                                 1639

<210> SEQ ID NO 3
<211> LENGTH: 6089
<212> TYPE: DNA
<213> ORGANISM: Artificial
<220> FEATURE:
<223> OTHER INFORMATION: Recombinant vector for human proinsulin
      expression

<400> SEQUENCE: 3
gacggatcgg gagatcttct agagagttct tctgtttgct agataagaaa tcctggtctg       60
ccatcccagc aggcccaggc tgtttaagtt actagataac agggttgtta ttgatcctat      120
tattattatt ttttctactc ttcctgattc cctgaagtcc aagggacgtt tttttctatt      180
aagaatgatt ttttgtttaa aaaaaaaaa agagtccttg ttgtgtcgct agctggtctg      240
tgacagatag agcccagagc tgcctcagtg ccctttactc aggagtggga gaacagaaag      300
taaataagcc agagcccaga gcactcttag tcatctggat ggctcagcgc tgggcccagc      360
acttgcaaat gctggctcct cccggactcc cctgttagcc ccatgttgtt aaccagttta      420
acattccctt atcacatgct catgtgggca gaattaagtg gaattagcta acaaattata      480
taaaattcat ttacctttaa actagtcgac accaaatcag gaacagaaag agtcaaggat      540 ccccaacca ctccaagtgg aggctgagaa aggttttgta gctgggtaga gtatgtacta       600
agagatggag acagctggct ctgagctctg aagcaagcac ctcttatgga gagttgctga      660
ccttcaggtg caaatctaag atactacagg agaatacacc atgggcttc agcccagttg       720 actcccgagt gggctatggg tttgtggaag agagataga agagaaggga cctttcttct       780
tgaattctgc tttccttcta cctctgaggg tgagctgggg tctcagctga ggtgaggaca      840
cagctatcag tgggaactgt gaaacaacag ttcaagggac aaagttacta ggtcccccaa      900
caactgcagc ctcctgggga tgatgtggaa aaatgctca gccaaggaca agaaggcct        960 caccctctct gagacaatgt cccctgctgt gaactggttc atcaggccac ccaggagccc     1020
ctattaagac tctaattacc ctaaggctaa gtagaggtgt tgttgtccaa tgagcacttt     1080
```

```
ctgcagacct agcaccaggc aagtgtttgg aaactgcagc ttcagcccct ctggccatct    1140
gctgatccac ccttaatggg acaaacagca aagtccaggg gtcaggggggg gggtgctttg    1200
gactataaag ctagtgggga ttcagtaacc cccagcccta agtgaccagc tacagtcgga    1260
aaccatcagc aagcaggtaa gcttgatatc ggtaccatgg ccctgtggat gcgcctcctg    1320
cccctgctgg cgctgctggc cctctgggga cctgacccag ccgcagcctt tgtgaaccaa    1380
cacctgtgcg gctcacacct ggtggaagct ctctacctag tgtgcgggga acgaggcttc    1440
ttctacacac ccaagacccg ccgggaggca gaggacctgc aggtggggca ggtggagctg    1500
ggcgggggcc ctggtgcagg cagcctgcag cccttggccc tggaggggtc cctgcagaag    1560
cgtggcattg tggaacaatg ctgtaccagc atctgctccc tctaccagct ggagaactac    1620
tgcaactagg cggccgcgtt taaactcgag gtctagaggg cccgtttaaa cccgctgatc    1680
agcctcgact gtgccttcta gttgccagcc atctgttgtt tgcccctccc ccgtgccttc    1740
cttgaccctg gaaggtgcca ctcccactgt ccttttcctaa taaaatgagg aaattgcatc    1800
gcattgtctg agtaggtgtc attctattct ggggggtggg gtggggcagg acagcaaggg    1860
ggaggattgg gaagacaata gcaggcatgc tggggatgcg gtgggctcta tggcttctga    1920
ggcggaaaga accagctggg gctctagggg gtatccccac gcgccctgta gcggcgcatt    1980
aagcgcggcg ggtgtggtgg ttacgcgcag cgtgaccgct acacttgcca gcgccctagc    2040
gcccgctcct ttcgctttct tcccttcctt tctcgccacg ttcgccggct ttccccgtca    2100
agctctaaat cgggggctcc ctttagggtt ccgatttagt gctttacggc acctcgaccc    2160
caaaaaactt gattagggtg atggttcacg tagtgggcca tcgccctgat agacggtttt    2220
tcgccctttg acgttggagt ccacgttctt taatagtgga ctcttgttcc aaactggaac    2280
aacactcaac cctatctcgg tctattcttt tgatttataa gggattttgc cgatttcggc    2340
ctattggtta aaaaatgagc tgatttaaca aaaatttaac gcgaattaat tctgtggaat    2400
gtgtgtcagt tagggtgtgg aaagtcccca ggctccccag caggcagaag tatgcaaagc    2460
atgcatctca attagtcagc aaccaggtgt ggaaagtccc caggctcccc agcaggcaga    2520
agtatgcaaa gcatgcatct caattagtca gcaaccatag tcccgcccct aactccgccc    2580
atcccgcccc taactccgcc cagttccgcc cattctccgc cccatggctg actaattttt    2640
tttatttatg cagaggccga ggccgcctct gcctctgagc tattccagaa gtagtgagga    2700
ggcttttttg gaggcctagg cttttgcaaa aagctcccgg gagcttgtat atccattttc    2760
ggatctgatc aagagacagg atgaggatcg tttcgcatga ttgaacaaga tggattgcac    2820
gcaggttctc cggccgcttg ggtggagagg ctattcggct atgactgggc acaacagaca    2880
atcggctgct ctgatgccgc cgtgttccgg ctgtcagcgc aggggcgccc ggttcttttt    2940
gtcaagaccg acctgtccgg tgccctgaat gaactgcagg acgaggcagc gcggctatcg    3000
tggctggcca cgacgggcgt tccttgcgca gctgtgctcg acgttgtcac tgaagcggga    3060
agggactggc tgctattggg cgaagtgccg gggcaggatc tcctgtcatc tcaccttgct    3120
cctgccgaga aagtatccat catggctgat gcaatgcggc ggctgcatac gcttgatccg    3180
gctacctgcc cattcgacca ccaagcgaaa catcgcatcg agcgagcacg tactcggatg    3240
gaagccggtc ttgtcgatca ggatgatctg gacgaagagc atcaggggct cgcgccagcc    3300
gaactgttcg ccaggctcaa ggcgcgcatg cccgacggcg aggatctcgt cgtgacccat    3360
ggcgatgcct gcttgccgaa tatcatggtg gaaaatggcc gcttttctgg attcatcgac    3420
tgtggccggc tgggtgtggc ggaccgctat caggacatag cgttggctac ccgtgatatt    3480
```

```
gctgaagagc ttggcggcga atgggctgac cgcttcctcg tgctttacgg tatcgccgct   3540
cccgattcgc agcgcatcgc cttctatcgc cttcttgacg agttcttctg agcgggactc   3600
tggggttcga aatgaccgac caagcgacgc ccaacctgcc atcacgagat ttcgattcca   3660
ccgccgcctt ctatgaaagg ttgggcttcg gaatcgtttt ccgggacgcc ggctggatga   3720
tcctccagcg cggggatctc atgctggagt tcttcgccca ccccaacttg tttattgcag   3780
cttataatgg ttacaaataa agcaatagca tcacaaattt cacaaataaa gcatttttt   3840 cactgcattc tagttgtggt ttgtccaaac tcatcaatgt atcttatcat gtctgtatac   3900
cgtcgacctc tagctagagc ttggcgtaat catggtcata gctgtttcct gtgtgaaatt   3960
gttatccgct cacaattcca cacaacatac gagccggaag cataaagtgt aaagcctggg   4020
gtgcctaatg agtgagctaa ctcacattaa ttgcgttgcg ctcactgccc gctttccagt   4080
cgggaaacct gtcgtgccag ctgcattaat gaatcggcca acgcgcgggg agaggcggtt   4140
tgcgtattgg gcgctcttcc gcttcctcgc tcactgactc gctgcgctcg tcgttcggc   4200 tgcggcgagc ggtatcagct cactcaaagg cggtaatacg gttatccaca gaatcagggg   4260
ataacgcagg aaagaacatg tgagcaaaag gccagcaaaa ggccaggaac cgtaaaaagg   4320
ccgcgttgct ggcgtttttc cataggctcc gcccccctga cgagcatcac aaaaatcgac   4380
gctcaagtca gaggtggcga aacccgacag gactataaag ataccaggcg tttccccctg   4440
gaagctccct cgtgcgctct cctgttccga ccctgccgct taccggatac ctgtccgcct   4500
ttctcccttc gggaagcgtg cgctttctc atagctcacg ctgtaggtat ctcagttcgg   4560
tgtaggtcgt tcgctccaag ctgggctgtg tgcacgaacc ccccgttcag cccgaccgct   4620
gcgccttatc cggtaactat cgtcttgagt ccaacccggt aagacacgac ttatcgccac   4680
tggcagcagc cactggtaac aggattagca gagcgaggta tgtaggcggt gctacagagt   4740
tcttgaagtg gtggcctaac tacggctaca ctagaagaac agtatttggt atctgcgctc   4800
tgctgaagcc agttaccttc ggaaaaagag ttggtagctc ttgatccggc aaacaaacca   4860
ccgctggtag cggtttttt gtttgcaagc agcagattac gcgcagaaaa aaggatctc   4920 aagaagatcc tttgatcttt tctacggggt ctgacgctca gtggaacgaa aactcacgtt   4980
aagggatttt ggtcatgaga ttatcaaaaa ggatcttcac ctagatcctt ttaaattaaa   5040
aatgaagttt taaatcaatc taagtatat atgagtaaac ttggtctgac agttaccaat   5100
gcttaatcag tgaggcacct atctcagcga tctgtctatt tcgttcatcc atagttgcct   5160
gactccccgt cgtgtagata actacgatac gggagggctt accatctggc cccagtgctg   5220
caatgatacc gcgagaccca cgctcaccgg ctccagattt atcagcaata aaccagccag   5280
ccggaagggc cgagcgcaga agtggtcctg caactttatc cgcctccatc cagtctatta   5340
attgttgccg ggaagctaga gtaagtagtt cgccagttaa tagtttgcgc aacgttgttg   5400
ccattgctac aggcatcgtg gtgtcacgct cgtcgtttgg tatggcttca ttcagctccg   5460
gttcccaacg atcaaggcga gttacatgat cccccatgtt gtgcaaaaaa gcggttagct   5520
ccttcggtcc tccgatcgtt gtcagaagta agttggccgc agtgttatca ctcatggtta   5580
tggcagcact gcataattct cttactgtca tgccatccgt aagatgcttt tctgtgactg   5640
gtgagtactc aaccaagtca ttctgagaat agtgtatgcg gcgaccgagt tgctcttgcc   5700
cggcgtcaat acgggataat accgcgccac atagcagaac tttaaaagtg ctcatcattg   5760
gaaaacgttc ttcggggcga aaactctcaa ggatcttacc gctgttgaga tccagttcga   5820
```

-continued

```
tgtaacccac tcgtgcaccc aactgatctt cagcatcttt tactttcacc agcgtttctg      5880
ggtgagcaaa acaggaagg caaaatgccg caaaaaggg aataagggcg acacggaaat        5940
gttgaatact catactcttc cttttcaat attattgaag catttatcag ggttattgtc       6000
tcatgagcgg atacatattt gaatgtattt agaaaaataa acaaataggg gttccgcgca      6060
catttccccg aaaagtgcca cctgacgtc                                        6089
```

<210> SEQ ID NO 4
<211> LENGTH: 14
<212> TYPE: PRT
<213> ORGANISM: Homo sapiens

<400> SEQUENCE: 4

Gly Gly Gly Pro Gly Ala Gly Ser Leu Gln Pro Leu Ala Leu
1               5                   10

<210> SEQ ID NO 5
<211> LENGTH: 20
<212> TYPE: DNA
<213> ORGANISM: Artificial
<220> FEATURE:
<223> OTHER INFORMATION: sgRNA coding DNA sequence

<400> SEQUENCE: 5

```
gctacacgcc caaggcccgt                                                     20
```

<210> SEQ ID NO 6
<211> LENGTH: 20
<212> TYPE: DNA
<213> ORGANISM: Artificial
<220> FEATURE:
<223> OTHER INFORMATION: gctacacgcc caaggcccgt

<400> SEQUENCE: 6

```
gccgcagaag cgtggcatcg                                                     20
```

<210> SEQ ID NO 7
<211> LENGTH: 9291
<212> TYPE: DNA
<213> ORGANISM: Artificial
<220> FEATURE:
<223> OTHER INFORMATION: Recombinant vector for pig proinsulin gene
      knockout

<400> SEQUENCE: 7

```
gagggcctat ttcccatgat tccttcatat ttgcatatac gatacaaggc tgttagagag       60
ataattggaa ttaatttgac tgtaaacaca agatattag tacaaaatac gtgacgtaga       120
aagtaataat ttcttgggta gtttgcagtt ttaaaattat gttttaaaat ggactatcat      180
atgcttaccg taacttgaaa gtatttcgat ttcttggctt tatatatctt gtggaaagga      240
cgaaacaccg ctacacgccc aaggcccgtg ttttagagct agaaatagca agttaaaata      300
aggctagtcc gttatcaact tgaaaaagtg caccgagtc ggtgcttttt tgttttagag       360
ctagaaatag caagttaaaa taaggctagt ccgtttttag cgcgtgcgcc aattctgcag      420
acaaatggct ctagaggtac ccgttacata acttacggta atggcccgc ctggctgacc       480 gcccaacgac ccccgcccat tgacgtcaat agtaacgcca atagggactt tccattgacg      540
tcaatgggtg gagtatttac ggtaaactgc ccacttggca gtacatcaag tgtatcatat      600
gccaagtacg cccctattg acgtcaatga cggtaaatgg cccgcctggc attgtgccca      660
gtacatgacc ttatgggact ttcctacttg gcagtacatc tacgtattag tcatcgctat      720
```

```
taccatggtc gaggtgagcc ccacgttctg cttcactctc ccatctccc ccccctcccc    780 accccaatt ttgtatttat ttatttttta attattttgt gcagcgatgg gggcggggg     840 gggggggggg cgcgcgccag gcggggcggg gcggggcgag gggcggggcg gggcgaggcg   900
gagaggtgcg gcggcagcca atcagagcgg cgcgctccga aagtttcctt ttatggcgag   960
gcggcggcgg cggcggccct ataaaaagcg aagcgcgcgg cgggcgggag tcgctgcgac  1020
gctgccttcg ccccgtgccc cgctccgccg ccgcctcgcg ccgcccgccc cggctctgac  1080
tgaccgcgtt actcccacag gtgagcgggc gggacggccc ttctcctccg ggctgtaatt  1140
agctgagcaa gaggtaaggg tttaagggat ggttggttgg tggggtatta atgtttaatt  1200
acctggagca cctgcctgaa atcactttt ttcaggttgg accggtgcca ccatggacta   1260
taaggaccac gacggagact acaaggatca tgatattgat tacaaagacg atgacgataa   1320
gatggcccca agaagaagc ggaaggtcgg tatccacgga gtcccagcag ccgacaagaa    1380
gtacagcatc ggcctggaca tcggcaccaa ctctgtgggc tgggccgtga tcaccgacga  1440
gtacaaggtg cccagcaaga aattcaaggt gctgggcaac accgaccggc acagcatcaa  1500
gaagaacctg atcggagccc tgctgttcga cagcggcgaa acagccgagg ccacccggct  1560
gaagagaacc gccagaagaa gatacaccag acggaagaac cggatctgct atctgcaaga  1620
gatcttcagc aacgagatgg ccaaggtgga cgacagcttc ttccacagac tggaagagtc  1680
cttcctggtg gaagaggata gaagcacga gcggcacccc atcttcggca acatcgtgga   1740
cgaggtggcc taccacgaga gtacccac catctaccac ctgagaaaga aactggtgga    1800
cagcaccgac aaggccgacc tgcggctgat ctatctggcc ctggcccaca tgatcaagtt  1860
ccggggccac ttcctgatcg agggcgacct gaaccccgac aacagcgacg tggacaagct  1920
gttcatccag ctggtgcaga cctacaacca gctgttcgag aaaaccccca tcaacgccag  1980
cggcgtggac gccaaggcca tcctgtctgc cagactgagc aagagcagac ggctggaaaa  2040
tctgatcgcc cagctgcccg gcgagaagaa gaatggcctg ttcggaaacc tgattgccct  2100
gagcctgggc ctgaccccca acttcaagag caacttcgac ctggccgagg atgccaaact  2160
gcagctgagc aaggacacct acgacgacga cctggacaac ctgctggccc agatcggcga  2220
ccagtacgcc gacctgtttc tggccgccaa gaacctgtcc gacgccatcc tgctgagcga  2280
catcctgaga gtgaacaccg agatcaccaa ggccccctg agcgcctcta tgatcaagag   2340
atacgacgag caccaccagg acctgaccct gctgaaagct ctcgtgcggc agcagctgcc  2400
tgagaagtac aaagagattt tcttcgacca gagcaagaac ggctacgccg gctacattga  2460
cggcggagcc agccaggaag agttctacaa gttcatcaag cccatcctgg aaaagatgga  2520
cggcaccgag gaactgctcg tgaagctgaa cagagaggac ctgctgcgga gcagcggac   2580 cttcgacaac ggcagcatcc ccaccagat ccacctggga gagctgcacg ccattctgcg    2640
gcggcaggaa gatttttacc cattcctgaa ggacaaccgg gaaagatcg agaagatcct    2700 gaccttccgc atcccctact acgtgggccc tctggccagg ggaaacagca gattcgcctg  2760
gatgaccaga aagagcgagg aaaccatcac cccctggaac ttcgaggaag tggtggacaa  2820
gggcgcttcc gcccagagct tcatcgagcg gatgaccaac ttcgataaga acctgcccaa  2880
cgagaaggtg ctgcccaagc acagcctgct gtacgagtac ttcaccgtgt ataacgagct  2940
gaccaaagtg aaatacgtga ccgagggaat gagaaagccc gccttcctga gcggcgagca  3000
gaaaaaggcc atcgtggacc tgctgttcaa gaccaaccgg aaagtgaccg tgaagcagct  3060
```

```
gaaagaggac tacttcaaga aaatcgagtg cttcgactcc gtggaaatct ccggcgtgga    3120
agatcggttc aacgcctccc tgggcacata ccacgatctg ctgaaaatta tcaaggacaa    3180
ggacttcctg gacaatgagg aaaacgagga cattctggaa gatatcgtgc tgaccctgac    3240
actgtttgag gacagagaga tgatcgagga acggctgaaa acctatgccc acctgttcga    3300
cgacaaagtg atgaagcagc tgaagcggcg gagatacacc ggctggggca ggctgagccg    3360
gaagctgatc aacggcatcc gggacaagca gtccggcaag acaatcctgg atttcctgaa    3420
gtccgacggc ttcgccaaca gaaacttcat gcagctgatc cacgacgaca gcctgacctt    3480
taaagaggac atccagaaag cccaggtgtc cggccagggc gatagcctgc acgagcacat    3540
tgccaatctg gccggcagcc ccgccattaa gaagggcatc ctgcagacag tgaaggtggt    3600
ggacgagctc gtgaaagtga tgggccggca caagcccgag aacatcgtga tcgaaatggc    3660
cagagagaac cagaccaccc agaagggaca gaagaacagc cgcgagagaa tgaagcggat    3720
cgaagagggc atcaaagagc tgggcagcca gatcctgaaa gaacacccg tggaaaacac    3780 ccagctgcag aacgagaagc tgtacctgta ctacctgcag aatgggcggg atatgtacgt    3840
ggaccaggaa ctggacatca accggctgtc cgactacgat gtggaccata tcgtgcctca    3900
gagctttctg aaggacgact ccatcgacaa caaggtgctg accagaagcg acaagaaccg    3960
gggcaagagc gacaacgtgc cctccgaaga ggtcgtgaag aagatgaaga actactggcg    4020
gcagctgctg aacgccaagc tgattaccca gagaaagttc gacaatctga ccaaggccga    4080
gagaggcggc ctgagcgaac tggataaggc cggcttcatc aagagacagc tggtggaaac    4140
ccggcagatc acaaagcacg tggcacagat cctggactcc cggatgaaca ctaagtacga    4200
cgagaatgac aagctgatcc gggaagtgaa agtgatcacc ctgaagtcca gctggtgtc    4260 cgatttccgg aaggatttcc agttttacaa agtgcgcgag atcaacaact accaccacgc    4320
ccacgacgcc tacctgaacg ccgtcgtggg aaccgccctg atcaaaaagt accctaagct    4380
ggaaagcgag ttcgtgtacg gcgactacaa ggtgtacgac gtgcggaaga tgatcgccaa    4440
gagcgagcag gaaatcggca aggctaccgc caagtacttc ttctacagca acatcatgaa    4500 cttttttcaag accgagatta ccctggccaa cggcgagatc cggaagcggc ctctgatcga    4560
gacaaacggc gaaaccgggg agatcgtgtg ggataagggc cgggattttg ccaccgtgcg    4620
gaaagtgctg agcatgcccc aagtgaatat cgtgaaaaag accgaggtgc agacaggcgg    4680
cttcagcaaa gagtctatcc tgcccaagag gaacagcgat aagctgatcg ccagaaagaa    4740
ggactgggac cctaagaagt acggcggctt cgacagcccc accgtggcct attctgtgct    4800
ggtggtggcc aaagtggaaa agggcaagtc caagaaactg aagagtgtga aagagctgct    4860
ggggatcacc atcatggaaa gaagcagctt cgagaagaat cccatcgact ttctggaagc    4920
caagggctac aaagaagtga aaaaggacct gatcatcaag ctgcctaagt actccctgtt    4980
cgagctggaa aacggccgga agagaatgct ggcctctgcc ggcgaactgc agaagggaaa    5040
cgaactggcc ctgcctcca atatgtgaa cttcctgtac ctggccagcc actatgagaa    5100
gctgaagggc tcccccgagg ataatgagca gaaacagctg tttgtggaac agcacaagca    5160
ctacctggac gagatcatcg agcagatcag cgagttctcc aagagagtga tcctggccga    5220
cgctaatctg gacaaagtgc tgtccgccta caacaagcac cgggataagc ccatcagaga    5280
gcaggccgag aatatcatcc acctgtttac cctgaccaat ctgggagccc tgccgccttt    5340
caagtacttt gacaccacca tcgaccggaa gaggtacacc agcaccaaag aggtgctgga    5400 cgccacccctg atccaccaga gcatcaccgg cctgtacgag acacggatcg acctgtctca    5460
```

```
gctgggaggc gacaaaaggc cggcggccac gaaaaaggcc ggccaggcaa aaagaaaaa    5520 ggaattcggc agtggagagg gcagaggaag tctgctaaca tgcggtgacg tcgaggagaa    5580
tcctggccca gtgagcaagg gcgaggagct gttcaccggg gtggtgccca tcctggtcga    5640
gctggacggg gacgtaaacg gccacaagtt cagcgtgtcc ggcgagggcg agggcgatgc    5700
cacctacggc aagctgaccc tgaagttcat ctgcaccacc ggcaagctgc ccgtgccctg    5760
gcccaccctc gtgaccaccc tgacctacgg cgtgcagtgc ttcagccgct accccgacca    5820
catgaagcag cacgacttct tcaagtccgc catgcccgaa ggctacgtcc aggagcgcac    5880
catcttcttc aaggacgacg gcaactacaa gacccgcgcc gaggtgaagt tcgagggcga    5940 cacccctggtg aaccgcatcg agctgaaggg catcgacttc aaggaggacg gcaacatcct    6000
ggggcacaag ctggagtaca actacaacag ccacaacgtc tatatcatgg ccgacaagca    6060
gaagaacggc atcaaggtga acttcaagat ccgccacaac atcgaggacg gcagcgtgca    6120
gctcgccgac cactaccagc agaacacccc catcggcgac ggccccgtgc tgctgcccga    6180
caaccactac ctgagcaccc agtccgccct gagcaaagac cccaacgaga gcgcgatca    6240 catggtcctg ctggagttcg tgaccgccgc cgggatcact ctcggcatgg acgagctgta    6300
caaggaattc taactagagc tcgctgatca gcctcgactg tgccttctag ttgccagcca    6360
tctgttgttt gccctccccc cgtgccttcc ttgaccctgg aaggtgccac tcccactgtc    6420 cttttcctaat aaaatgagga aattgcatcg cattgtctga gtaggtgtca ttctattctg    6480
gggggtgggg tggggcagga cagcaagggg gaggattggg aagagaatag caggcatgct    6540
ggggagcggc cgcaggaacc cctagtgatg gagttggcca ctccctctct gcgcgctcgc    6600
tcgctcactg aggccgggcg accaaaggtc gcccgacgcc cgggctttgc ccgggcggcc    6660
tcagtgagcg agcgagcgcg cagctgcctg caggggcgcc tgatgcggta ttttctcctt    6720
acgcatctgt gcggtatttc acaccgcata cgtcaaagca accatagtac gcgccctgta    6780
gcggcgcatt aagcgcggcg ggtgtggtgg ttacgcgcag cgtgaccgct acacttgcca    6840
gcgccctagc gcccgctcct ttcgctttct tcccttcctt tctcgccacg ttcgccggct    6900
ttccccgtca agctctaaat cggggcctcc ctttagggtt ccgatttagt gctttacggc    6960
acctcgaccc caaaaaactt gatttgggtg atggttcacg tagtgggcca tcgccctgat    7020
agacggtttt tcgccctttg acgttggagt ccacgttctt taatagtgga ctcttgttcc    7080
aaactggaac aacactcaac cctatctcgg gctattcttt tgatttataa gggattttgc    7140
cgatttcggc ctattggtta aaaaatgagc tgatttaaca aaaatttaac gcgaattta    7200 acaaaatatt aacgtttaca attttatggt gcactctcag tacaatctgc tctgatgccg    7260
catagttaag ccagccccga cacccgccaa caccgctga cgcgccctga cgggcttgtc    7320
tgctcccggc atccgcttac agacaagctg tgaccgtctc cgggagctgc atgtgtcaga    7380
ggttttcacc gtcatcaccg aaacgcgcga cgaaaggg cctcgtgata cgcctatttt    7440
tataggttaa tgtcatgata taatggttt cttagacgtc aggtggcact tttcggggaa    7500
atgtgcgcgg aacccctatt tgttattttt ctaaataca ttcaaatatg tatccgctca    7560
tgagacaata accctgataa atgcttcaat aatattgaaa aaggaagagt atgagtattc    7620
aacatttccg tgtcgccctt attccctttt ttgcggcatt ttgccttcct gtttttgctc    7680
acccagaaac gctggtgaaa gtaaaagatg ctgaagatca gttgggtgca cgagtgggtt    7740
acatcgaact ggatctcaac agcggtaaga tccttgagag ttttcgcccc gaagaacgtt    7800
```

-continued

```
ttccaatgat gagcactttt aaagttctgc tatgtggcgc ggtattatcc cgtattgacg      7860
ccgggcaaga gcaactcggt cgccgcatac actattctca gaatgacttg gttgagtact      7920
caccagtcac agaaaagcat cttacggatg gcatgacagt aagagaatta tgcagtgctg      7980
ccataaccat gagtgataac actgcggcca acttacttct gacaacgatc ggaggaccga      8040
aggagctaac cgcttttttg cacaacatgg gggatcatgt aactcgcctt gatcgttggg      8100
aaccggagct gaatgaagcc ataccaaacg acgagcgtga caccacgatg cctgtagcaa      8160
tggcaacaac gttgcgcaaa ctattaactg gcgaactact tactctagct tcccggcaac      8220
aattaataga ctggatggag gcggataaag ttgcaggacc acttctgcgc tcggcccttc      8280
cggctggctg gtttattgct gataaatctg gagccggtga gcgtggaagc cgcggtatca      8340
ttgcagcact ggggccagat ggtaagccct cccgtatcgt agttatctac acgacgggga      8400
gtcaggcaac tatggatgaa cgaaatagac agatcgctga gataggtgcc tcactgatta      8460
agcattggta actgtcagac caagtttact catatatact ttagattgat ttaaaacttc      8520 attttttaatt taaaaggatc taggtgaaga tccttttga taatctcatg accaaaatcc      8580
cttaacgtga gttttcgttc cactgagcgt cagaccccgt agaaaagatc aaaggatctt      8640
cttgagatcc ttttttttctg cgcgtaatct gctgcttgca acaaaaaaaa ccaccgctac      8700
cagcggtggt ttgtttgccg gatcaagagc taccaactct ttttccgaag gtaactggct      8760
tcagcagagc gcagatacca aatactgtcc ttctagtgta gccgtagtta ggccaccact      8820
tcaagaactc tgtagcaccg cctacatacc tcgctctgct aatcctgtta ccagtggctg      8880
ctgccagtgg cgataagtcg tgtcttaccg ggttggactc aagacgatag ttaccggata      8940
aggcgcagcg gtcgggctga acggggggtt cgtgcacaca gcccagcttg gagcgaacga      9000
cctacaccga actgagatac ctacagcgtg agctatgaga aagcgccacg cttcccgaag      9060
ggagaaaggc ggacaggtat ccggtaagcg gcagggtcgg aacaggagag cgcacgaggg      9120
agcttccagg gggaaacgcc tggtatcttt atagtcctgt cgggtttcgc cacctctgac      9180
ttgagcgtcg attttttgtga tgctcgtcag gggggcggag cctatggaaa aacgccagca      9240
acgcggcctt tttacggttc ctggcctttt gctggccttt tgctcacatg t              9291
```

<210> SEQ ID NO 8
<211> LENGTH: 19
<212> TYPE: DNA
<213> ORGANISM: Artificial
<220> FEATURE:
<223> OTHER INFORMATION: 1st PCR forward

<400> SEQUENCE: 8

```
ctcctctctc ggagcccttt                                                  19
```

<210> SEQ ID NO 9
<211> LENGTH: 19
<212> TYPE: DNA
<213> ORGANISM: Artificial
<220> FEATURE:
<223> OTHER INFORMATION: 1st PCR reverse

<400> SEQUENCE: 9

```
ttattgggtt ttggggtgc                                                   19
```

<210> SEQ ID NO 10
<211> LENGTH: 18
<212> TYPE: DNA
<213> ORGANISM: Artificial

```
<220> FEATURE:
<223> OTHER INFORMATION: 2nd PCR forward

<400> SEQUENCE: 10
gtcccccagg tcctcacc                                              18

<210> SEQ ID NO 11
<211> LENGTH: 18
<212> TYPE: DNA
<213> ORGANISM: Artificial
<220> FEATURE:
<223> OTHER INFORMATION: 2nd PCR reverse

<400> SEQUENCE: 11
cccaccctgg agtggaag                                              18

<210> SEQ ID NO 12
<211> LENGTH: 23
<212> TYPE: DNA
<213> ORGANISM: Artificial
<220> FEATURE:
<223> OTHER INFORMATION: hINS CDS forward

<400> SEQUENCE: 12
atggccctgt ggatgcgcct cct                                        23

<210> SEQ ID NO 13
<211> LENGTH: 23
<212> TYPE: DNA
<213> ORGANISM: Artificial
<220> FEATURE:
<223> OTHER INFORMATION: hINS CDS reverse

<400> SEQUENCE: 13
ctagttgcag tagttctcca gct                                        23
```

TRANSGENIC CLONED PIGLET EXPRESSING HUMAN PROINSULIN AND METHOD OF PRODUCING THE SAME

CROSS-REFERENCE TO RELATED APPLICATIONS

This application is based on and claims priority from Korean Patent Application No. 10-2017-0124507, filed on Sep. 26, 2017, with the Korean Intellectual Property Office, the disclosure of which is incorporated herein in its entirety by reference.

TECHNICAL FIELD

The present disclosure relates to a transgenic cloned piglet expressing human proinsulin and a method of preparing the same, and more particularly, to a recombinant vector for human proinsulin expression, a transformed cell line into which the recombinant vector is introduced, a transgenic cloned piglet expressing human proinsulin and a method of producing the same.

BACKGROUND

Diabetes Mellitus is a disease which has hyperglycemia and its complications caused by abnormal insulin secretion in the pancreatic β-cell, an abnormal acting organ for the insulin or an abnormal receptor of the organ. For treatment of Diabetes Mellitus, insulin injections, exercise, and dieting are commonly used. However, it is an inextricable disease, and there is still a risk of complications.

In recent, diabetes is treated with pancreas and pancreatic islet transplantation. The pancreas transplantation has issues such as absolute lack of donor, high surgical complication and post-transplant management difficulties including continued administration of the immunosuppressive drug. On the other hand, the pancreatic islet transplantation is a relatively simple procedure for transplantation without complications, compared to the pancreas transplantation and induces immune tolerance through pre-operative immune regulation of the pancreatic islet so that it can be expected to lower the side effects due to the use of immunosuppressive drugs. Further, there is an advantage in that the isolated islet is cultured and maintained in vitro to perform the transplantation at an appropriate time. However, there is a problem that the number of the available human pancreas is too few to perform the islet transplantation clinically.

In order to address the issue, various methods of proliferation of human islets are disclosed to include in vitro proliferation of pancreatic β-cells, induction of differentiation of islet cells which are adult stem cells, induction of differentiation of embryonic stem cells, proliferation of fetal islets as well as xenotransplantation using animal tissue other than human is disclosed. Pigs are known to be an animal for the ideal source of the xenotransplantation. This is why the insulin of pigs has been used for the human body without side effects for a long time, the insulin metabolism of pigs is similar to the human body, pigs are widely used for edible purposes to lessen resistance and relatively easy to handle the same, and pigs have a significant number of islets. Despite the advantages as described, the xenotransplantation using the pancreatic islets of pigs has not been applied to the treatment of diabetes due to the difficulty of isolating islets as well as xenograft rejection.

SUMMARY

In order to address the issues of the prior art as described above, the present inventors have developed a transgenic cloned piglet in which the porcine proinsulin is removed, and the human proinsulin gene is expressed. Further, the present disclosure has been completed by confirming that the human proinsulin is expressed in the body of this transgenic cloned piglet.

The present disclosure has been made in an effort to provide a recombinant vector for human proinsulin expression.

Further, the present disclosure has been made in an effort to provide a transformed cell line prepared by introducing the recombinant vector for human proinsulin expression.

Further, the present disclosure has been made in an effort to provide a transgenic cloned piglet expressing the human proinsulin and a method of preparing the same.

In order to achieve the objects, an exemplary embodiment of the present disclosure provides the recombinant vector for human proinsulin expression including a human proinsulin gene represented by the nucleotide sequence of SEQ ID NO: 1, an enhancer and a promoter.

Another exemplary embodiment of the present disclosure provides a transformed cell line prepared by introducing the recombinant vector for human proinsulin expression into somatic cells.

Yet Another exemplary embodiment of the present disclosure provides a method of producing a transgenic cloned piglet expressing the human proinsulin, which includes nuclear-transferring the transformed cell line into a denucleated oocyte to prepare a reconstituted oocyte and transplanting the reconstituted oocyte into a fallopian tube of a surrogate.

Still Another exemplary embodiment of the present disclosure provides a transgenic cloned piglet produced according to the method of producing the transgenic cloned piglet expressing the human proinsulin.

According to the exemplary embodiments of the present disclosure, the transgenic cloned piglet expressing human proinsulin has 4 and 36 bases deleted in the porcine proinsulin gene locus, the human proinsulin coding sequence has the genotype inserted into the porcine genome, and the human proinsulin is generally expressed in the body of such transgenic cloned piglet. These indicate that the transgenic cloned piglet can be used as a raw animal for the xeno-islet transplantation. The transgenic cloned piglet expressing the human proinsulin gene of the present disclosure can be used in various fields such as the field of prevention or treatment of diabetes and complications caused thereby through the human proinsulin production as well as the field of xenotransplantation.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
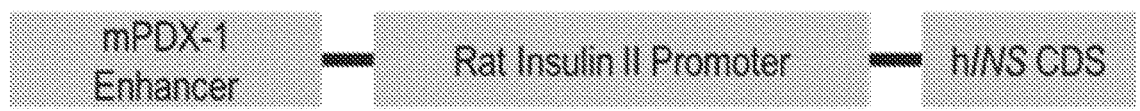
FIG. 1 is a schematic diagram of a human proinsulin nucleotide fragment according to the present disclosure.

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, the present disclosure is described in detail.

According to an aspect of the present disclosure, the present disclosure provides the recombinant vector for human proinsulin expression, which includes a human proinsulin gene represented by the nucleotide sequence of SEQ ID NO: 1, an enhancer and a promoter.

In the present disclosure, "proinsulin" refers to a precursor of insulin produced in pancreatic β-cells of the islet of Langerhans in the pancreas, which consists of A and B chains and the C-peptide linking them. Further, the proinsulin is synthesized in rough endoplasmic reticulum of cells and is cleaved at the Golgi body to divide into C-peptide and insulin including A and B chains.

In the present disclosure, the sequence encoding human proinsulin is preferably represented by the nucleotide sequence of SEQ ID NO: 1. Further, the recombinant vector for human proinsulin expression may include functional equivalents of the human proinsulin represented by the nucleotide sequence of SEQ ID NO: 1. The term "functional equivalent" refers to one having sequence homology of at least 70%, preferably at least 80%, more preferably at least 90%, further more preferably at least 95% compared with the nucleotide sequence of SEQ ID NO: 1, which is caused by the results of base deletion, substitution, and insertion and thus means a polynucleotide having substantially the same physiological activity as a polynucleotide represented by the nucleotide sequence of SEQ ID NO: 1. "% of sequence homology" to polynucleotides is confirmed by comparing the comparison region and two optimally aligned sequences, and a portion of the polynucleotide sequence in the comparison region may include the addition or deletion (that is, gap) compared to the reference sequence (without addition or deletion) for the optimal alignment of the two sequences.

In the present disclosure, the term "vector" refers to a gene product including a nucleotide sequence operably linked to a suitable regulatory sequence so that the target gene can be expressed in a suitable host, and the regulatory sequence may include a promoter being capable of initiating transcription, any operator sequences for modulating such transcription and sequences regulating the termination of translation and transcription. The vector of the present disclosure is not particularly limited as long as it is capable of being cloned in cells and may include any vector known in the art. For example, it may be a plasmid, a cosmid, a phage particle or a viral vector.

In the present disclosure, the term "recombinant vector" may be used as a vector that can express the target polypeptide at a high efficiency in a suitable host cell when the coding gene of the target polypeptide to be expressed is operatively linked, which can be expressed in host cells. The host cell may preferably be a eukaryotic cell. An expression regulatory sequence such as a promoter, a terminator and an enhancer, a sequence for membrane targeting or secretion can be suitably selected depending on the type of the host cell and can be variously combined according to the purpose.

In the present disclosure, the term "promoter" refers to a DNA sequence site to which transcriptional regulatory factors bind, which is intended to induce overexpression of the target gene. Examples of the promoter include Pribnow box, TATA box, and the like.

In one embodiment of the present disclosure, the promoter of a rat insulin II gene is used as a promoter.

In the present disclosure, the term "enhancer" is a site that induces structural changes in a DNA template to make the transcription more active. The enhancer is represented by a unique nucleotide sequence to each gene and promotes transcription at any site in the gene.

In one embodiment of the present disclosure, an enhancer of a mouse PDX-1 gene is used as an enhancer.

In the present disclosure, it is preferable that the recombinant vector is represented by the nucleotide sequence of SEQ ID NO: 3, which is an illustrative example only and the present disclosure is not limited thereto.

Figure 11:
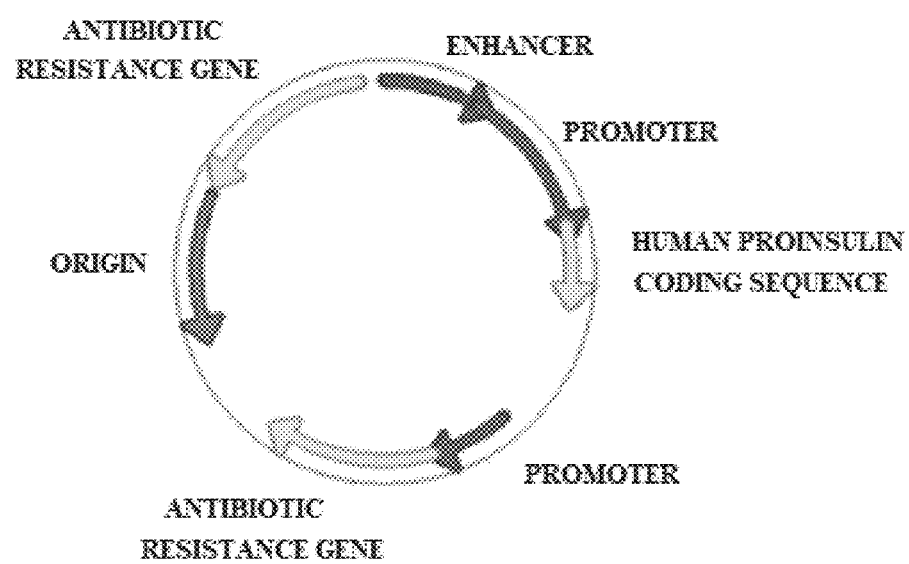
FIG. 11 illustrates a vector map of a recombinant vector of the present invention.

In the present disclosure, the recombinant vector has a vector map as exhibited in FIG. 11. As long as the recombinant vector has the constitution of a vector capable of expressing the human proinsulin of the present disclosure, the present disclosure is not limited thereto.

According to another aspect of the present disclosure, the present disclosure provides a transformed cell line prepared by introducing the recombinant vector for human proinsulin expression into somatic cells.

The transformed cell line is preferably further transformed by an INS (insulin) gene knockout recombinant vector. More specifically, the INS gene knockout recombinant vector is introduced into the somatic cells for primary transformation. The recombinant vector for expressing human proinsulin is introduced into the primary transformed somatic cell for secondary transformation. Thus, the secondary transformed cell line can be produced. Further, the two vectors may be sequentially introduced into somatic cells as described above or may be simultaneously introduced into somatic cells to result in the transformation. However, the present invention is not limited thereto. The INS gene knockout recombinant vector is intended to remove porcine proinsulin, which includes Cas9 gene and a nucleotide sequence encoding sgRNA represented by SEQ ID NO.: 5 or 6, preferably represented by SEQ ID NO.: 7, but the present disclosure is not limited thereto.

In the present disclosure, the term "cell line" refers to each individual of the cell system when the cells are separated, cultured and sub-cultured in which the cell line can be distinguished from other cell lines by genetic traits, and the original genetic trait is maintained during the sub-culture.

In the present disclosure, the cell line may be an oocyte cell line, a fibroblast cell line or a renal cell line, preferably a fibroblast cell line. More specifically, a fetal-derived cell line is used as a cell line. A primary cell line may be used at one time. Thus, a primary renal cell line or a primary fibroblast line is more preferably used as the cell line of the present disclosure. The primary fibroblast cell line is most preferably used.

In the present disclosure, the term "transformation" refers to the change in the genetic properties of a living organism caused by DNA given from outside, which is also referred to as transfection, transfiguration, or conversion. In other words, "transformation" means introducing a gene into a host cell so that the gene may be expressed in the host cell.

In the method for introducing the recombinant vector for human proinsulin expression of the present disclosure into cell lines to result in the transformation, it may be transformed by introducing the same into eukaryotic cells using conventional methods such as nucleofection, transient transfection, microinjection, transduction, cell fusion, calcium phosphate precipitation, liposome-mediated transfection, DEAE dextran-mediated transfection, polybrene-mediated transfection, and electroporation.

In one embodiment of the present disclosure, after the primary transformation, the recombinant vector for human proinsulin expression is introduced into the primary transformed cell line by the nucleofection to prepare the secondary transformed cell line.

In the present disclosure, the transformed cell line was deposited at the Korean Cell Line Bank on Sep. 6, 2017, and accession number KCLRF-BP-00408 was received.

According to still another aspect of the present disclosure, the present disclosure provides a method of producing a transgenic cloned piglet expressing human proinsulin, which includes nuclear-transferring the transformed cell line into a denucleated oocyte to prepare a reconstituted oocyte and transplanting the reconstituted oocyte into a fallopian tube of a surrogate.

In the present disclosure, the method of producing the transgenic cloned piglet may further include, before nuclear-transferring, preparing a vector for human proinsulin expression, introducing the proinsulin expression vector into somatic cells to prepare a transformed cell line, and denucleating an oocyte.

In the present disclosure, the term "denucleated oocyte" refers to an oocyte from which the nucleus has been removed.

In the present disclosure, the term "nuclear-transfer" refers to a genetic engineering technique in which cells without nucleus are artificially combined with nuclei of other cells to have the same traits and is preferably performed by methods known in the art.

According to yet another aspect of the present disclosure, a transgenic cloned piglet prepared according to the method of producing a transgenic cloned piglet expressing human proinsulin is provided. The transgenic cloned piglet has 4 and 36 bases deleted in the porcine proinsulin gene locus and has a genotype in which the human proinsulin coding sequence is inserted into in the porcine genome.

Therefore, the transgenic cloned piglet expressing the human proinsulin gene according to the present disclosure may be used not only in the field of xenotransplantation but also in the field of prevention and treatment of diabetes and its complications through human proinsulin production.

Hereinafter, the present disclosure will be described in more detail with reference to examples. It is apparent to those skilled in the art that these examples are merely illustrative of the present disclosure and that the scope of the present disclosure is not to be construed as limited by these examples.

Example 1. Construction of Recombinant Vector Expressing Human Proinsulin

For the human proinsulin expression, a human proinsulin nucleotide fragment including an enhancer and a promoter was synthesized and inserted into a plasmid vector to construct a recombinant vector for human proinsulin expression.

1-1. Synthesis of Human Proinsulin Nucleotide Fragment

The human proinsulin nucleotide fragment was synthesized using the human proinsulin coding sequence (CDS) represented by the nucleotide sequence of SEQ ID NO: 1, the mouse PDX-1 gene enhancer, and the rat insulin II promoter. Specifically, the human proinsulin nucleotide fragment was designed in which the rat insulin II promoter was linked to the 3' terminal of the PDX-1 enhancer, and the human proinsulin coding sequence was linked to the 3' terminal of the rat insulin II promoter, which was synthesized by the method known in the art. The human proinsulin nucleotide fragment is represented by SEQ ID NO: 2, and a schematic diagram thereof is illustrated in FIG. 1.

1-2. Construction of Recombinant Vector for Human Proinsulin Expression

The human proinsulin nucleotide fragment prepared in Example 1-1 was inserted into pCAG 1.1 vector using restriction enzymes BglII and XhoI (New England Biolabs, MA, USA).

Figure 2:
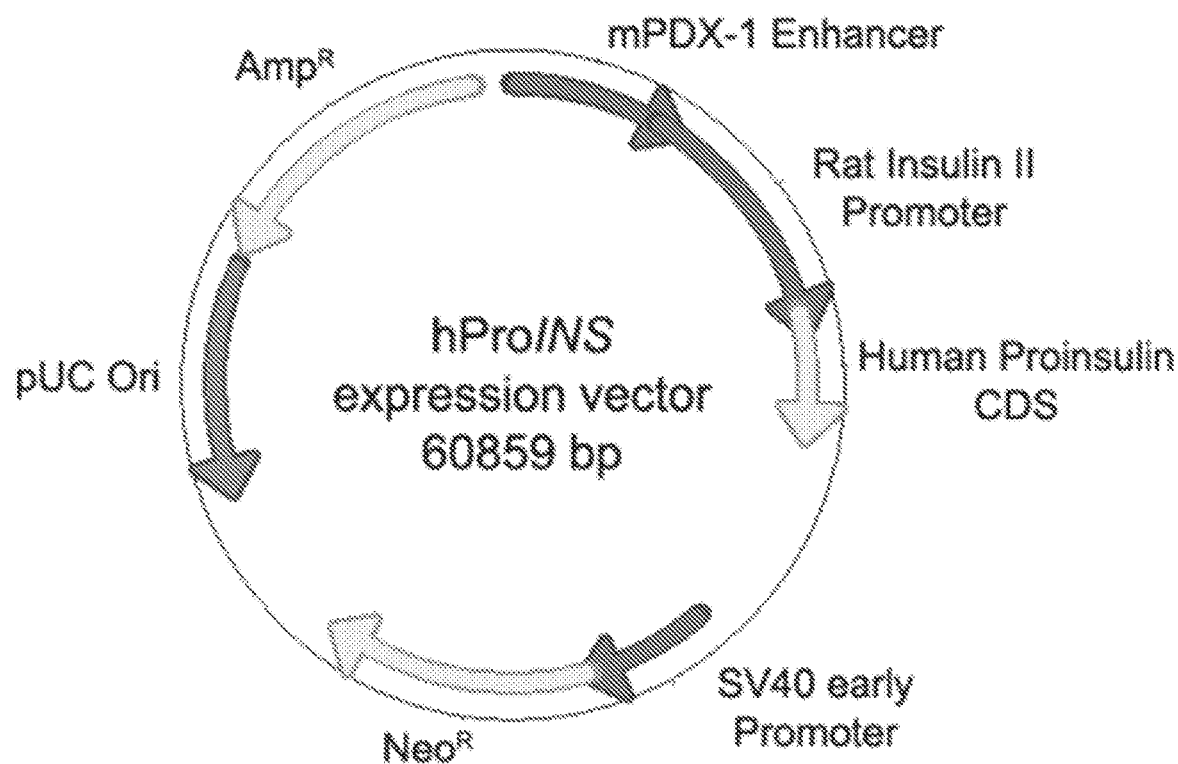
FIG. 2 illustrates a vector map of a recombinant vector for human proinsulin expression according to the present disclosure.

The recombinant vector for human proinsulin expression constructed by the process as described above is represented by the nucleotide sequence of SEQ ID NO: 3, and its vector map and the position of each gene are illustrated in FIG. 2.

Example 2. Production of Proinsulin Knockout Piglet

Figure 3:
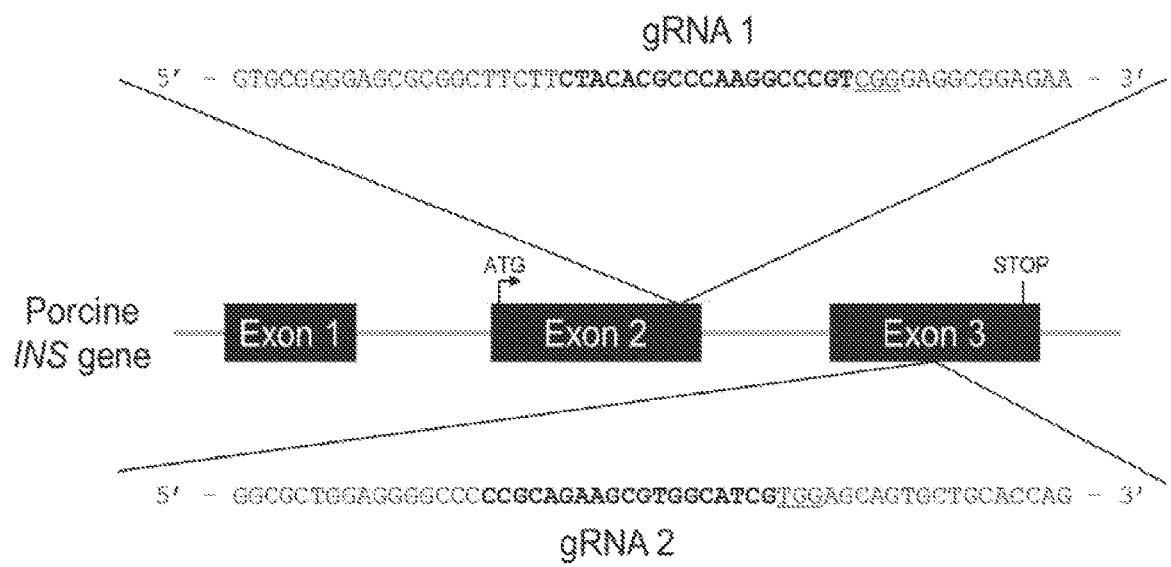
FIG. 3 is a diagram illustrating sequences of an INS gene targeted by an INS (insulin) gene knockout recombinant vector.
Figure 4:
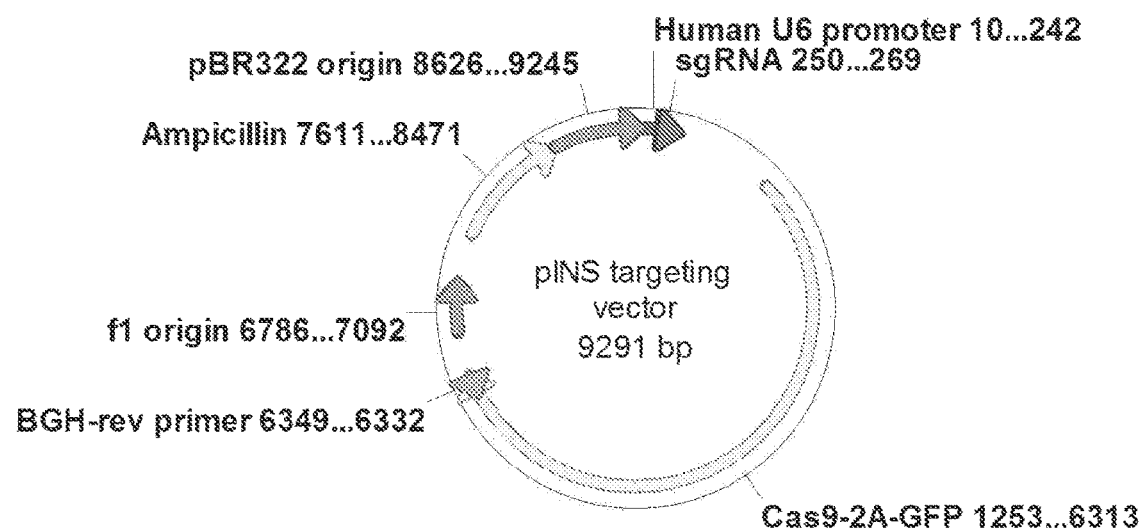
FIG. 4 illustrates a vector map of an INS gene knockout recombinant vector.

For the production of proinsulin knockout piglet, INS (insulin) gene knockout recombinant vector including sgRNA (small guide RNA) and Cas9 gene represented by the nucleotide sequence of SEQ ID NO: 5 or 6 was prepared using CRISPR/Cas 9 system. The prepared INS gene recombinant vector targets the sequence in the porcine INS gene, and each sgRNA-targeting sequence is illustrated in FIG. 3. The INS gene knockout recombinant vector is represented by the nucleotide sequence of SEQ ID NO: 7, and its vector map is illustrated in FIG. 4.

The INS gene knockout recombinant vector was introduced into a fibroblast using Nucleofector™ (LONZA, Basel, Switzerland) for primary genetic modification. The fibroblast was isolated from PWG micropig and maintained in DMEM (Biowest, Nuaille, France) medium including 20% fetal bovine serum and 1% penicillin-streptomycin (Gibco, CA, USA) under a condition of 5% carbon dioxide and 37° C. After 48 hours of transfection, cell sorting was performed using a cell sorter. The sorted cell was seeded and cultured using a limiting dilution method to prepare single cell-derived transformed cell line. The INS gene knockout cell line was used as a donor cell for somatic cell nuclear transfer (SCNT).

In order to transplant the nuclei into somatic cells, a denucleated oocyte was prepared. The INS gene knockout cell line was inserted into the prepared denucleated oocyte, and an electric pulse was applied to prepare a reconstructed oocyte. The denucleated oocyte was transplanted into the fallopian tube of a surrogate, and about 114 days later, the proinsulin knockout piglet was taken out of the surrogate by a C-section.

The produced proinsulin knockout piglet is characterized in which all or part of the DNA strand encoding the INS gene is modified so that the porcine insulin is not expressed.

Example 3. Preparation of Secondary Genetically Modified Cell Expressing Human Proinsulin The porcine primary fibroblast was isolated from the proinsulin knockout piglet produced in Example 2 as described above. The porcine primary fibroblast was cultured in DMEM (Biowest, Nuaille, France) medium including 20% fetal bovine serum and 1% penicillin-streptomycin (Gibco, CA, USA) under a condition of 5% carbon dioxide and 37° C.

For the secondary genetic modification of the INS gene knockout porcine primary fibroblast, the recombinant vector for human proinsulin expression constructed in Example 1 was introduced into the porcine primary fibroblast using Nucleofector™ (LONZA, Basel, Switzerland) for the secondary genetic modification. After 42 hours from the introduction of the recombinant vector into the porcine primary fibroblast, the transgenic cells were cultured for 2 weeks in the presence of neomycin (G418) to select a genetically modified cell line having antibiotic resistance. The secondary genetically modified cell line was used as a donor cell for somatic cell nuclear transfer (SCNT).

The donor cell line produced by the process as described above has the properties of knocking out the porcine proinsulin (primary genetic modification) and expressing human proinsulin (secondary genetic modification), and it was deposited at the Korean Cell Line Bank on Sep. 6, 2017, and accession number KCLRF-BP-00408 was received.

Example 4. Production of Transgenic Cloned Piglet Expressing Human Proinsulin Gene 4-1. Used Pig The pigs used as surrogate mothers were raised in Mgenplus Co., Ltd., Korea. All animal experiments were approved by Institutional Animal Care and Use Committee (IACUC) of Mgenplus Co., Ltd., and the following all experimental procedures using pigs were conducted according to the guidelines of the Commission. The surgical procedure was performed under general anesthesia and proceeded to reduce the pain of the animal as far as possible. The pigs were reared under normal livestock conditions.

4-2. Production of Oocytes for Somatic Cell Nuclear Transfer

To prepare the denucleated oocyte, porcine oocytes collected from the local slaughterhouse were transferred to the laboratory with a condition of the temperature of 25° C. to 30° C. and sodium chloride (NaCl) of 0.9% (w/v). The oocytes were obtained from an antral follicle (3 mm to 6 mm in diameter) and cultured in the mature medium at 5% carbon dioxide and 39° C. After 44 hours of incubation, the matured oocytes were placed in the manipulation medium supplemented with cytochalasin B (5 mg/ml stock, 1.5 μm per 10 ml manipulation medium), and the first polar body and adjacent cytoplasm were removed to result in denucleation using a thin glass pipette (diameter 20 μm). The denucleated oocytes were used as nuclear donor cells on somatic cell nuclear transfer (SCNT).

4-3. Somatic Cell Nuclear Transfer

One donor cell including the human proinsulin gene of Example 3 was injected into the perivitelline space of the denucleated oocyte prepared in Example 4-2. In the Example, the cell membrane of the donor cell was in contact with the cytoplasmic membrane of the denucleated oocyte. The donor cell-injected oocyte was placed between two platinum electrodes, and an electrical pulse (BTX, two 1.1 kV/cm DC pulses for 60 microseconds) was applied to the two platinum electrodes. As a result, the cytoplasmic membrane of the donor cell and the cytoplasmic membrane of the denucleated oocyte were fused. The reconstituted embryo due to electrical pulses was cultured in PZM3 medium with 0.5 μM Scriptaid, a histone deacetylase inhibitor, at 39° C. and 5% carbon dioxide for 14 hours to 16 hours.

4-4. Production of Transgenic Cloned Piglet

The reconstructed embryos (average 310) prepared in Example 4-3 were transplanted into each of 5 surrogate mothers, and 4 surrogate mothers among them were pregnant. About 114 days after pregnancy, C-section was performed to take out 17 transgenic cloned piglets (including 6 stillborn babies) from the surrogate mothers.

Example 5. Analysis of Genotype of Transgenic Cloned Piglet

For the genotype analysis of the transgenic cloned piglets produced in Example 4, a tail biopsy was performed on each transgenic cloned piglet on the day of birth to obtain a genomic DNA extraction sample thereof. The genomic DNA was extracted from the genomic DNA extraction sample using a genomic DNA extraction kit (iNtRon Biotechnology, Seongnam, Korea) according to the manufacturer's manual. In order to confirm genetic modification of porcine proinsulin gene, PCR on the porcine proinsulin gene locus was performed using Pfu plus 5× master mix (ELPIS biotech, Daejeon, Korea). The primers illustrated in Table 1 as described below were used for the PCR.

TABLE 1

|  | Nucleotide sequence (5'→3') | Predicted Product Size (bp) |
| --- | --- | --- |
| 1st PCR forward (SEQ ID NO: 8) | CTCCTCTCTCGGAGCCCTT | 865 |
| 1st PCR reverse (SEQ ID NO: 9) | TTATTGGGTTTTGGGGTGC | 865 |

TABLE 1-continued

| | Nucleotide sequence (5'→3') | Predicted Product Size (bp) |
|---|---|---|
| 2nd PCR (Nested PCR) forward (SEQ ID NO: 10) | GTCCCCCAGGTCCTCACC | 558 |
| 2nd PCR (Nested PCR) reverse (SEQ ID NO: 11) | CCCACCCTGGAGTGGAAG | 558 |
| hINS CDS forward (SEQ ID NO: 12) | ATGGCCCTGTGGATGCGCCTCCT | Human: 333 Piglet: 718 |
| hINS CDS reverse (SEQ ID NO: 13) | CTAGTTGCAGTAGTTCTCCAGCT | Human: 333 Piglet: 718 |

T7 endonuclease I (T7E I) assay and sequencing of the PCR products were carried out, and the results thereof are illustrated in FIG. 5. Further, the addition of the human proinsulin coding sequence (CDS) of the transgenic cloned piglet genome was confirmed using the PCR product, and the results thereof are illustrated in FIG. 6. Wild-type pigs and INS gene targeted pigs (pINS KO) were used as control groups.

Figures 5A, 5B:
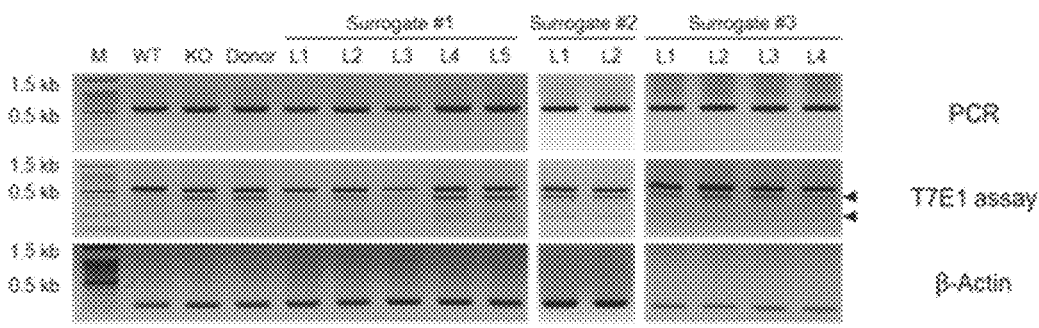
FIG. 5A illustrates the results of analysis of T7 endonuclease I of transgenic cloned piglets expressing human proinsulin according to the present disclosure.
FIG. 5B illustrates the results of sequencing of T7 endonuclease I of transgenic cloned piglets expressing human proinsulin according to the present disclosure.
Figure 6:
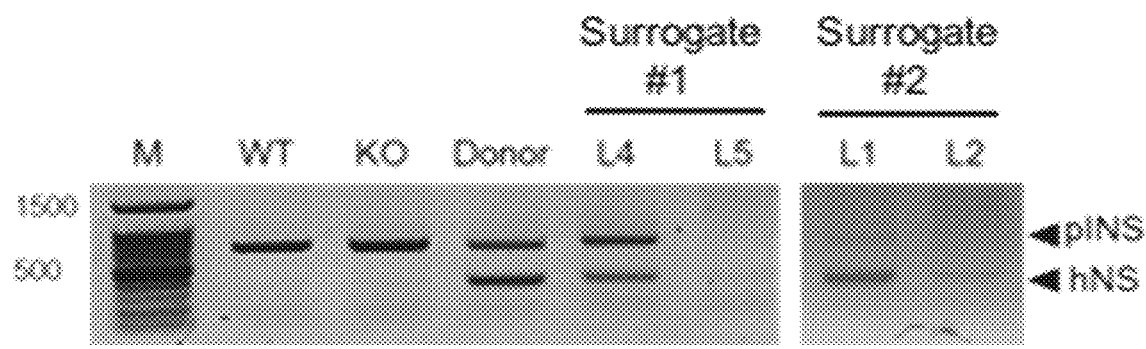
FIG. 6 illustrates the results of confirming insertion of a human proinsulin coding sequence into a transgenic cloned piglet expressing human proinsulin according to the present disclosure.

As illustrated in FIG. 5A, the transgenic cloned piglet according to the present disclosure exhibited a change in the porcine proinsulin gene locus and exhibited the same cleavage pattern as the genomic DNA of the INS gene knockout pig and donor cells. Further, the results of the sequencing illustrated in FIG. 5B indicates that the transgenic cloned piglet according to the present disclosure exhibited deletion of the same base in the porcine proinsulin gene locus thereas, and 4 bases and 36 bases, respectively, were deleted in alleles.

As illustrated in FIG. 6, bands of human proinsulin and porcine proinsulin were confirmed in the transgenic cloned piglet according to the present disclosure, which appears to be due to the similarity of sequences of human and pig primers. The results indicate that the human proinsulin coding sequence has a length of about 0.3 kb without an intron and the porcine proinsulin has a length of about 0.7 kb with an intron. Further, it was confirmed that #1-L4, #1-L5, #2-L1, and #2-L2 of the transgenic cloned piglets exhibited human proinsulin coding sequences and genomic DNA of porcine proinsulin.

Therefore, it was confirmed that the genotypes of #1-L4, #1-L5, #2-L1, and #2-L2 of the transgenic cloned piglets are such that 4 and 36 bases were deleted in the porcine proinsulin gene locus, and the human proinsulin coding sequence was inserted into the porcine genome.

Figure 7:
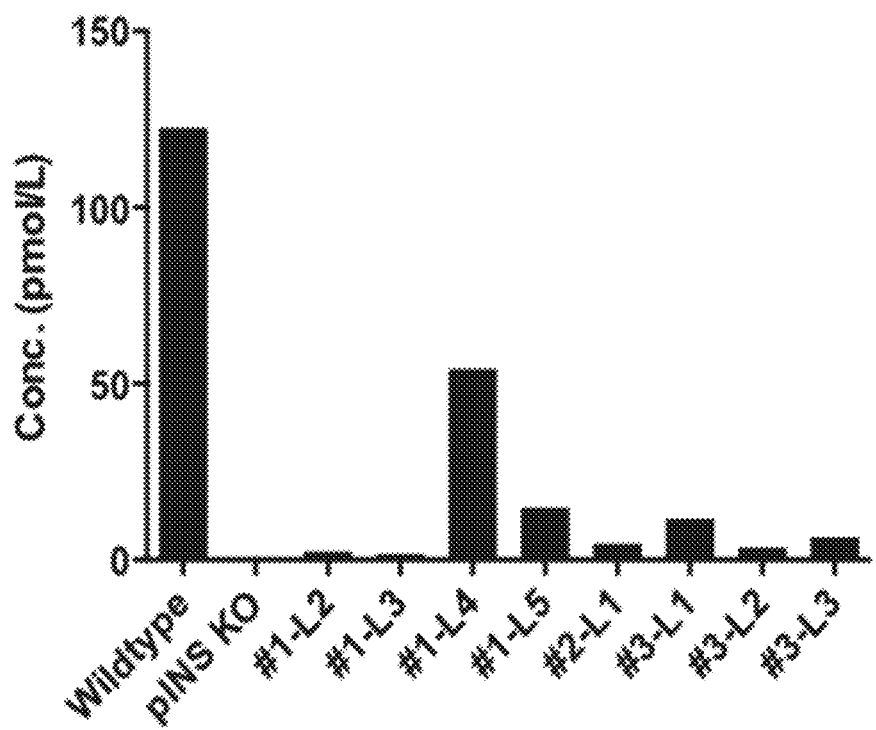
FIG. 7 illustrates the results of measuring insulin level in serum of a transgenic cloned piglet expressing human proinsulin according to the present disclosure.

Example 6. Phenotypic Analysis of Transgenic Cloned Piglet 6-1. Measurement of Insulin Concentration in Serum The blood of the transgenic cloned piglet was collected to measure the concentration of insulin included in the serum of the transgenic cloned piglet prepared in Example 4. The collected blood was centrifuged to separate the serum. The human insulin concentration of the serum was measured using an insulin ELISA kit (Mercodia, Uppsala, Sweden). The result of measuring the insulin concentration of the serum is illustrated in FIG. 7. Wild-type pigs and INS gene targeted pigs (pINS KO) were used as control groups.

As illustrated in FIG. 7, insulin was detected in the serum of the transgenic cloned piglets #1-L2, #1-L3, #1-L4, #1-L5, #2-L1, #3-L1, #3-L2, and #3-L3. In particular, the insulin concentration of #1-L4 was the highest. Further, insulin was not detected in the INS gene targeted pig (pINS KO), which was the control group.

6-2. Immunohistochemical (IHC) Analysis

Figure 8:
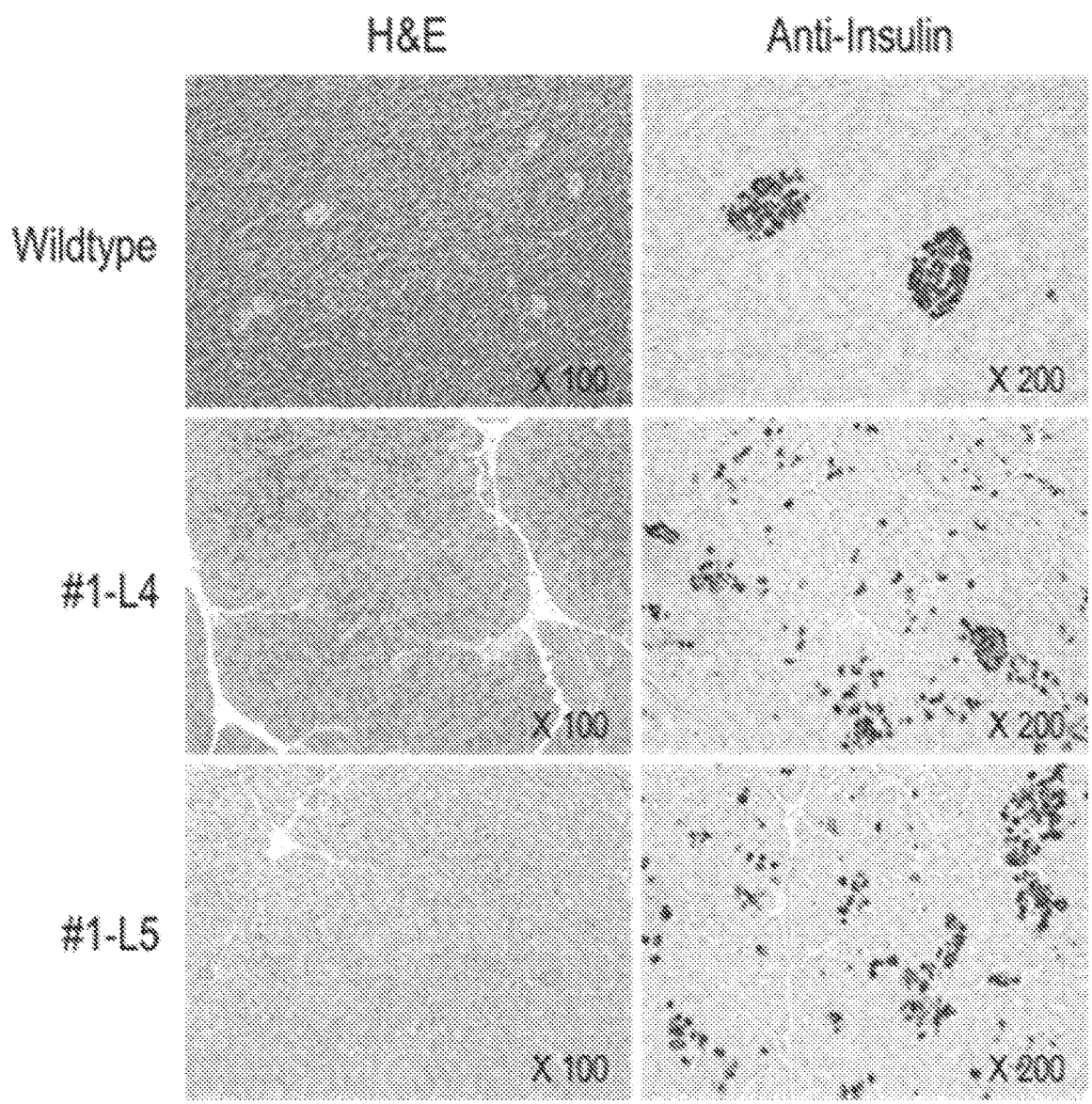
FIG. 8 illustrates the results of immunohistochemically analyzing pancreatic β-cells of a transgenic cloned piglet expressing human proinsulin according to the present disclosure.

Immunohistochemical analysis was performed on the pancreatic β-cells of the transgenic cloned piglet in order to confirm the insulin of the transgenic cloned piglet prepared in Example 3. First, the pancreas was isolated from the transgenic cloned piglet and fixed in 10% neutral buffered formalin. The fixed tissue was placed in paraffin to produce a paraffin block, and the paraffin block was divided into two pieces. One of the divided paraffin blocks was H&E stained with a conventional H&E staining kit, and mouse anti-swine insulin (AbD Serotec, Kidlington, UK) was added to the other paraffin block. These were observed with a microscope, and the results are illustrated in FIG. 8. Wild-type pig was used as a control group.

As illustrated in FIG. 8, it was confirmed that insulin was highly expressed in pancreatic β-cells of the transgenic cloned piglets #1-L4 and #1-L5.

6-3. Measurement of Blood Glucose Level

Figure 9:
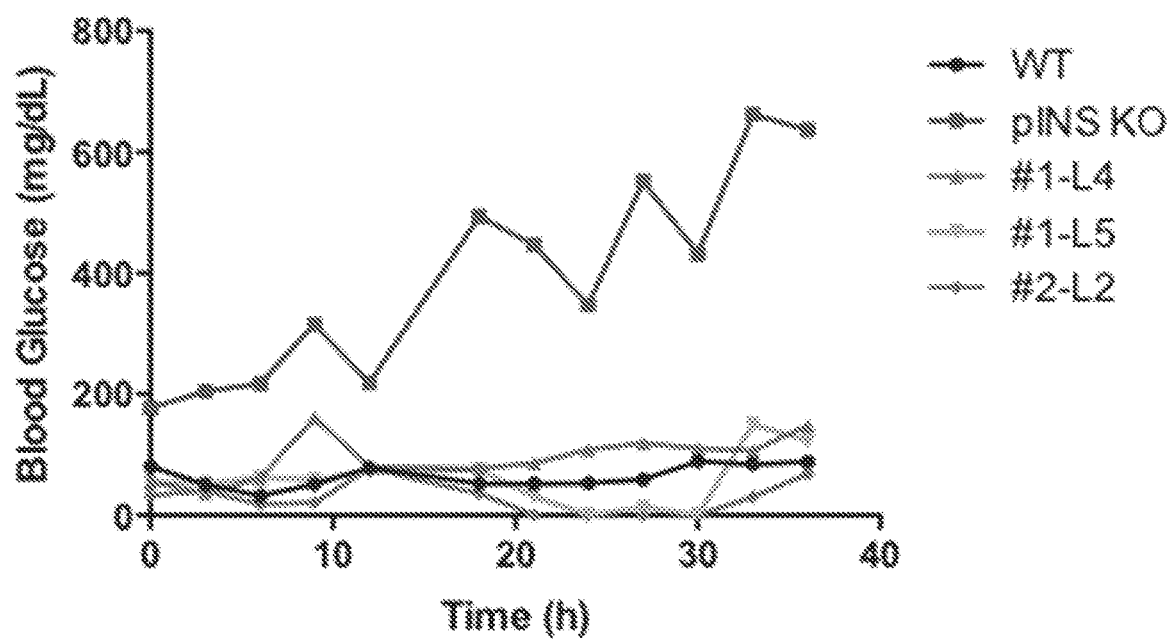
FIG. 9 illustrates the results of measuring blood glucose level of a transgenic cloned piglet expressing human proinsulin according to the present disclosure.

Non-fasting blood glucose level of insulin of the transgenic cloned piglet produced in Example 3 was measured using ACCU-CHEK® blood glucose meter (Roche, Ind., USA). For the measurement of non-blood glucose level, the transgenic cloned piglet was fed, and the blood thereof was collected every 3 hours. The result of blood glucose measurement of the transgenic cloned piglet is illustrated in FIG. 9. Wild-type pigs and INS gene targeted pigs (pINS KO) were used as control groups.

As illustrated in FIG. 9, blood glucose levels of the transgenic cloned piglets #1-L4, #1-L5 and #2-L2 with high insulin level in the serum, were measured to be similar to that of the wild-type pig.

6-4. Peptide Analysis of Protein Lysate from Pancreas

Peptide analysis of the protein lysate collected from the pancreas of the transgenic cloned piglet produced in Example 4 was performed. Specifically, SDS-PAGE of the protein lysate collected from the transgenic cloned piglet was conducted, and the target size gel (about 10 kDa) was separated. The separated gel was analyzed using LC-MS/MS, and then the sequence of human proinsulin peptide was confirmed. The results of peptide analysis of the pancreatic protein lysate are illustrated in FIG. 10.

Figure 10:
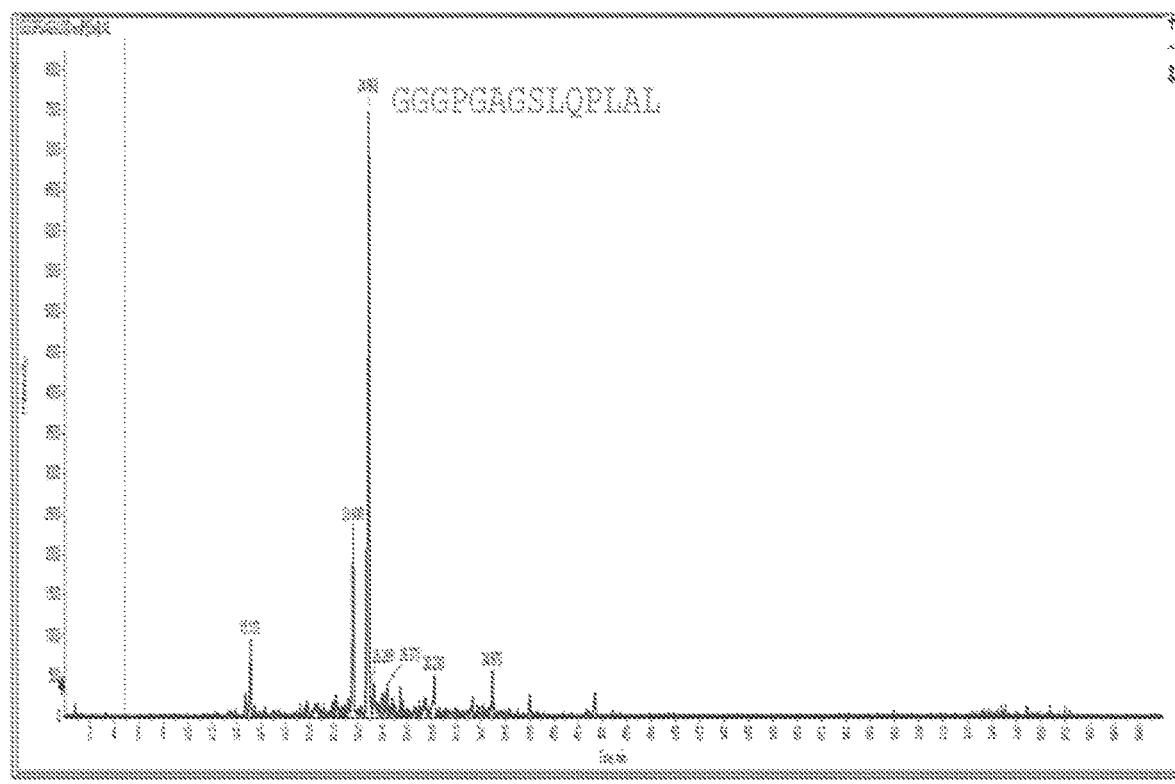
FIG. 10 illustrates the results of separating pancreatic protein lysates from a transgenic cloned piglet expressing the human proinsulin according to the present disclosure to analyze peptides thereof.

As illustrated in FIG. 10, the peptide with the highest concentration included in the pancreatic protein lysate of the transgenic cloned piglet was detected 25 minutes after the start of the analysis. The result of sequence analysis of the detected peptide indicates that the peptide was a human proinsulin C-peptide represented by the amino acid sequence of SEQ ID NO: 4.

In conclusion, the results as described above indicate that the transgenic cloned piglet expressing human proinsulin according to the present disclosure has 4 and 36 bases deleted in the porcine proinsulin gene locus, the human proinsulin coding sequence has the genotype inserted into the porcine genome, and the human proinsulin is expressed in the body of such transgenic cloned piglet. These indicate that the transgenic cloned piglet can be used as a source animal for the xeno-islet transplantation. The transgenic cloned piglet expressing the human proinsulin gene of the present disclosure can be used in various fields such as xenotransplantation, human proinsulin production, prevention or treatment of diabetes and complications.

From the foregoing, specific portions of the present disclosure have been described in detail. However, it will be apparent by those of ordinary skill in the art that this specific description is merely for preferred embodiments and that the scope of the present disclosure is not limited thereby. Therefore, the substantive scope of the present disclosure is to be defined by the appended claims and their equivalents.

[Access Number]
Name of depositor: Korean Cell Line Bank
Accession number: KCLRF-BP-00408
Date of accession: Sep. 6, 2017

The ASCII text file "Sequence.txt" created on Jul. 9, 2018, having the size of 24 KB, is incorporated by reference into the specification.

What is claimed is:

1. A method of producing a transgenic, cloned piglet expressing human proinsulin, the method comprising:
   genetically modifying
   a porcine nuclear donor cell by:
   introducing into the cell a first recombinant vector encoding a sgRNA and Cas9 wherein said first recombinant vector results in knockout of the porcine insulin gene in the genome of the cell, thereby forming a first genetically modified porcine donor cell,
   transferring the nucleus from the first genetically modified porcine donor cell into a first denucleated porcine oocyte by electrofusing and activating a cell couplet comprising the first genetically modified donor cell and first denucleated porcine oocyte to form a first porcine embryo,
   transplanting the first porcine embryo to the fallopian tube of a porcine surrogate mother to produce a first transgenic, cloned piglet that fails to express porcine proinsulin,
   isolating a somatic cell from the first transgenic cloned piglet and introducing into said cell from the first transgenic piglet a second recombinant vector encoding human proinsulin operably linked to the rat insulin II gene promoter and mouse PDX-1 enhancer, thereby forming a second genetically modified porcine donor cell,
   transferring the nucleus from the second genetically modified porcine donor cell into a second denucleated porcine oocyte by electrofusing and activating a cell couplet comprising the second genetically modified porcine donor cell and second denucleated porcine oocyte to form a second porcine embryo,
   transplanting the second porcine embryo to the fallopian tube of a porcine surrogate mother to produce a transgenic cloned piglet that fails to express porcine proinsulin and that expresses human proinsulin.

2. The method of claim 1, wherein the second recombinant vector encoding human proinsulin is set forth by SEQ ID NO: 3.

3. The method of claim 1, wherein the sgRNA is encoded by the nucleotide sequence set forth in SEQ ID NO: 5 or 6.

4. The method of claim 1, wherein the first recombinant vector comprises the sequence set forth by SEQ ID NO: 7.

5. The method of claim 1, wherein the somatic cell is a fibroblast.

6. The method of claim 1, wherein the second genetically modified porcine donor cell is deposited as Accession No. KCLRF-BP-00408.

7. A transgenic cloned piglet expressing human proinsulin, the transgenic cloned piglet being produced by the method of claim 1.

* * * * *